US00PP17392P2

(12) United States Plant Patent
Oudshoorn

(10) Patent No.: US PP17,392 P2
(45) Date of Patent: Jan. 30, 2007

(54) *LYCHNIS* PLANT NAMED 'ROLLY'S FAVORITE'

(50) Latin Name: *Lychnis hybrid*
Varietal Denomination: Rolly's Favorite

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 35 days.

(21) Appl. No.: 11/151,914

(22) Filed: Jun. 14, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Lychnis* plant named 'Rolly's Favorite', characterized by its upright and somewhat outwardly spreading plant habit; freely basal clumping growth habit; dense and bushy plants; freely flowering habit; and bright red purple-colored flowers.

2 Drawing Sheets

Botanical designation: *Lychnis hybrida.*
Cultivar denomination: 'Rolly's Favorite'.

BACKGROUND OF THE INVENTION

The present Invention relates to a new and distinct cultivar of *Lychnis* plant, botanically known as *Lychnis flos-jovis,* and hereinafter referred to by the cultivar name 'Rolly's Favorite'.

The new *Lychnis* originated from a chance cross-pollination in 1998 of an unnamed selection of *Lychnis flos-jovis,* not patented, as the female, or seed, parent with an unknown selection of *Lychnis flos-jovis* as the male, or pollen, parent. The cultivar Rolly's Favorite was discovered and selected by the Inventor as a flowering plant within the progeny of the state cross-pollination in a controlled environment in 2000 in Rijpwetering, The Netherlands.

Asexual reproduction of the new cultivar by cuttings at Rijpwetering, The Netherlands, since 2001, has shown that the unique features of this new *Lychnis* are stable and reproduced true to type in successive generations.

SUMMARY OF THE INVENTION

Plants of the cultivar Rolly's Favorite have not been observed under all possible environmental conditions. The phenotype may vary somewhat with variations in environment such as temperature and light intensity without, however, any variance in genotype.

The following traits have been repeatedly observed and are determined to be the unique characteristics of 'Rolly's Favorite'. These characteristics in combination distinguish 'Rolly's Favorite' as a new and distinct cultivar:

1. Upright and somewhat outwardly spreading plant habit.
2. Freely basal clumping growth habit, dense and bushy plants.
3. Freely flowering habit.
4. Bright red purple-colored flowers.

Plants of the new *Lychnis* differ from plants of the female parent selection in the following characteristics:

1. Plants of the new *Lychnis* are stronger than plants of the female parent selection.
2. Flower color of plants of the new *Lychnis* was more intense than flower color of plants of the female parent selection.

Plants of the new *Lychnis* can be compared to plants of the *Lychnis* cultivar Lychjen, disclosed in U.S. Plant Pat. No. 14,139. In side-by-side comparisons conducted in Rijpwetering, The Netherlands, plants of the new *Lychnis* differed from plants of the cultivar Lychjen in the following characteristics:

1. Plants of the new *Lychnis* were more compact than plants of the cultivar Lychjen.
2. Plants of the new *Lychnis* had shorter leaves than plants of the cultivar Lychjen.
3. Plants of the new *Lychnis* had single flowers whereas plants of the cultivar Lychjen had double flowers.
4. Flowers of plants of the new *Lychnis* were darker in color than flowers of plants of the cultivar Lychjen.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Lychnis.*

The photograph on the first sheet comprises a side perspective view of typical plants of 'Rolly's Favorite' grown in a container.

The photograph at the top of the second sheet comprises a close-up view of typical flowers of 'Rolly's Favorite'.

The photograph at the bottom of the second sheet is a close-up view of typical flower bud and leaves of 'Rolly's Favorite'.

DETAILED BOTANICAL DESCRIPTION

In the following description, color references are made to The Royal Horticultural Society Colour Chart, 2001 Edition, except where general terms of ordinary dictionary significance are used. Plants were grown during the spring in Rijpwetering, The Netherlands under outdoor field conditions which closely approximate commercial production conditions. During the production of the plants, day temperatures ranged from 7 to 20° C. and night temperatures ranged from 1 to 10° C. Plants used for the photographs and description were grown for two growing seasons.

Botanical classification: *Lychnis flos-jovis* cultivar Rolly's Favorite.

Parentage:

*Female, or seed, parent.*—Unnamed selection of *Lychnis flos-jovis,* not patented.

*Male, or pollen, parent.*—Unknown selection of *Lychnis flos-jovis,* not patented.

Propagation:

*Type.*—By cuttings.

*Time to initiate roots.*—About one month at 15° C.

*Root description.*—Fibrous, fine; whitish brown in color.

*Rooting habit.*—Freely branching.

Plant description:

*Plant form.*—Upright and somewhat outwardly spreading; freely basal clumping perennial; dense and bushy plants; leaves, basal; flowering stems arise from the root crown.

*Usage.*—Appropriate for use as a border plant and in containers. Plant height, soil level to top of flowers: About 44 cm.

*Plant width.*—About 53 cm.

*Branch description.*—Quantity per plant: About 39. Length: About 27.1 cm. Diameter: About 4 mm. Internode length: About 6.7 cm. Texture: Densely pubescent. Strength: Strong. Color: 144A.

*Foliage description.*—Arrangement: Basal or opposite; sessile. Length: About 6.6 cm. Width: About 3.5 cm. Shape: Ovate. Apex: Acute to slightly apiculate. Base: Cuneate. Margin: Entire. Texture, upper and lower surfaces: Densely pubescent. Venation pattern: Pinnate. Color: Developing foliage, upper surface: 137A to 137B; towards the base, 144B to 144C. Developing foliage, lower surface: 138A to 138B; towards the base, 144C. Fully expanded foliage, upper surface: 137A; towards the base, 144A to 144B. Fully expanded foliage, lower surface: 137C; towards the base, 143A. Venation, upper surface: 137A. Venation, lower surface: 143A to 143B.

Flower description:

*Flower type and habit.*—Single flowers arranged in terminal compound cymes. Flowering stems, erect to slightly outwardly spreading; flowers face upright, outwardly or drooping. Flowers not persistent.

*Fragrance.*—None detected.

*Natural flowering season.*—Continuously flowering from late spring to early summer in The Netherlands.

*Quantity.*—Freely flowering with about 42 flowers and flower buds per flowering stem; about 1,600 flowers and flower buds per plant.

*Flower longevity.*—Flowers last about one week on the plant.

*Inflorescence height.*—About 18.2 cm.

*Inflorescence diameter.*—About 13.8 cm.

*Flower diameter.*—About 2.7 cm.

*Flower depth (height).*—About 2.3 cm.

*Flower buds.*—Length: About 1.3 cm. Diameter: About 4 mm. Shape: Elliptic. Texture: Densely pubescent. Color: 183B; towards the base, 183C to 183D.

*Petals.*—Arrangement: About five petals fused into a slightly flattened tube. Length: About 3 cm. Width: About 1.4 cm. Shape: Spatulate. Apex: Retuse. Margin: Entire. Texture, upper and lower surfaces: Smooth; satiny. Color: When opening, upper surface: N74B. When opening, lower surface: 72C. Fully opened, upper surface: 73A; color becoming closer to N78A with development. Fully opened, lower surface: N74C. Throat and tube: Initially 145D; color becoming closer to 157B with development.

*Petaloids.*—Arrangement: About five petaloids at the base of each petal. Length: About 2 mm. Width: About 3 mm. Shape: Spatulate. Apex: Praemorse. Margin: Entire. Texture, upper and lower surfaces: Smooth; satiny. Color: When opening, upper and lower surfaces: N155A. Fully opened, upper and lower surfaces: N155A.

*Sepals.*—Arrangement: About five sepals fused into a tubular calyx. Length: About 1.7 cm. Diameter: About 1.5 mm. Apex: Acute. Margin: Entire. Texture, upper and lower surfaces: Pubescent. Color: When opening, upper surface: 146B to 146C; stripes, 183D. When opening, lower surface: 183B; towards the base, 183C to 183D. Fully opened, upper surface: 146D; stripes, 183B to 183C. Fully opened, lower surface: 187B to 187C.

*Peduncles.*—Length: About 13.5 cm. Diameter: About 3 cm. Strength: Strong. Angle: Erect to about 20° from vertical. Texture: Smooth, glabrous. Color: 146A to 146B; towards the apex, tinted with 187A.

*Pedicels.*—Length: About 4 cm. Diameter: About 1 mm. Strength: Moderately strong. Angle: About 25° from vertical. Texture: Smooth, glabrous. Color: 144B.

*Reproductive organs.*—Stamens: Quantity per flower: About ten. Filament length: About 1.2 cm. Filament color: Close to 155A. Anther length: About 1.5 mm. Anther shape: Narrowly oblong. Anther color: 155A. Pollen amount: Moderate. Pollen color: Lighter than 155A. Pistils: No pistils observed.

*Seed/fruit.*—Seed and fruit production have not been observed.

Disease/pest resistance: Under commercial production conditions, plants of the new *Lychnis* have not been noted to be resistant to pathogens or pests common to *Lychnis.*

Garden performance: Plants of the new *Lychnis* have been observed to tolerate rain and wind. Plants of the *Lychnis* have been observed to be tolerant to USDA Hardiness Zone 5 and to tolerate temperatures as high as 30° C.

It is claimed:

1. A new and distinct cultivar of *Lychnis* plant named 'Rolly's Favorite', as illustrated and described.

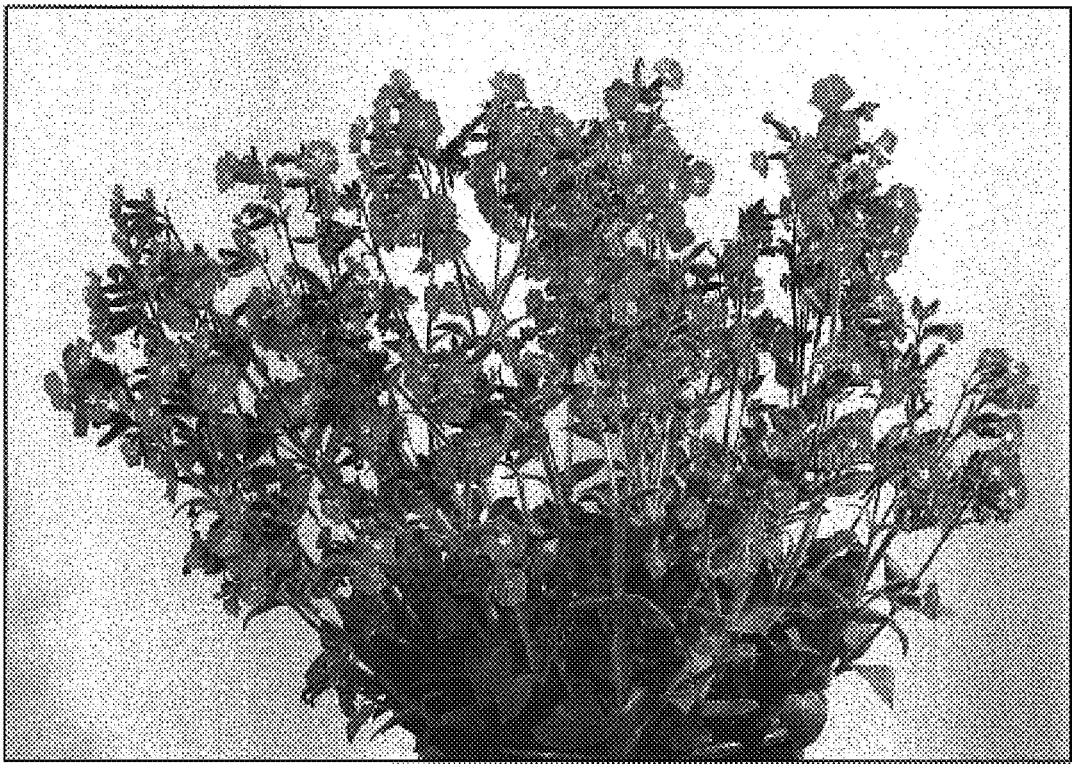

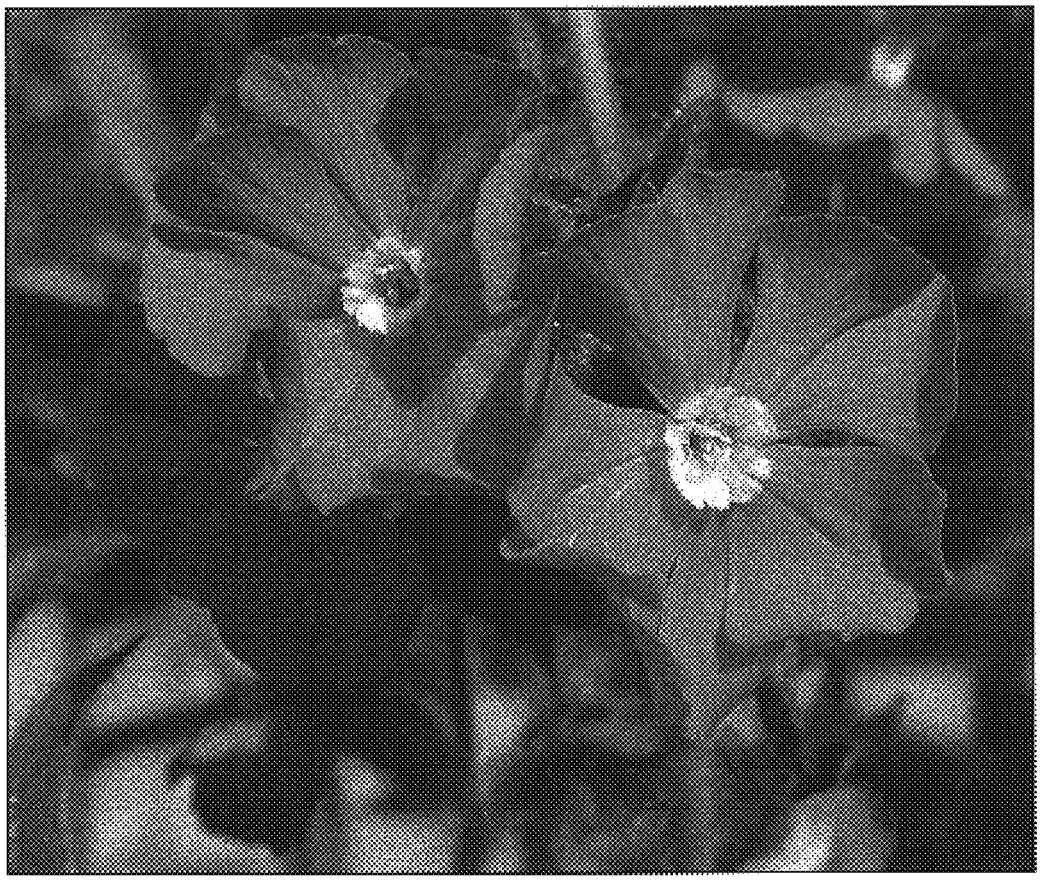
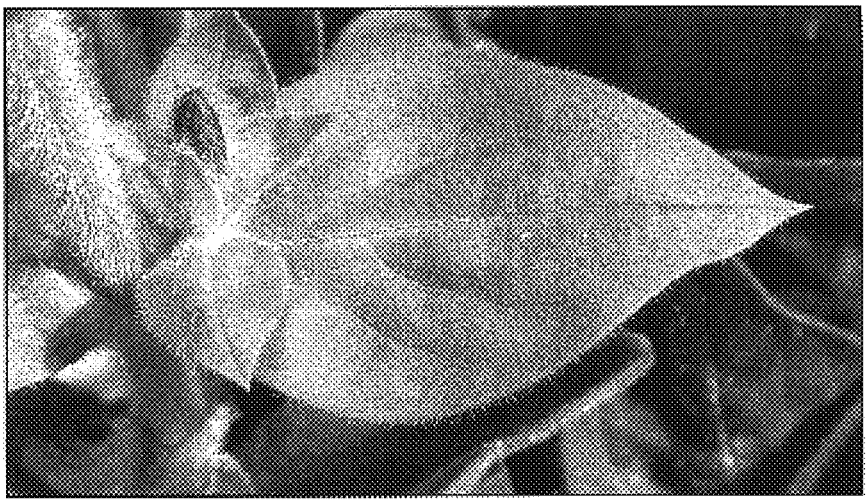

* * * * *